United States Patent
Lee et al.

(10) Patent No.: US 8,059,489 B1
(45) Date of Patent: Nov. 15, 2011

(54) ACOUSTIC AIRPORT SURVEILLANCE SYSTEM

(75) Inventors: Jonathan S. Lee, Irvine, CA (US);
Richard O. Nielsen, Anaheim, CA (US);
Henry Hooper Davis, Irvine, CA (US);
Paul H. Dunholter, Corona del Mar, CA (US)

(73) Assignee: The Boeing Company, Chicago, IL (US)

( * ) Notice: Subject to any disclaimer, the term of this patent is extended or adjusted under 35 U.S.C. 154(b) by 343 days.

(21) Appl. No.: 12/426,100

(22) Filed: Apr. 17, 2009

(51) Int. Cl.
  *G01N 29/14* (2006.01)
  *G01S 1/00* (2006.01)
  *G01S 3/80* (2006.01)

(52) U.S. Cl. ...... 367/136

(58) Field of Classification Search ........ 367/136, 367/127
See application file for complete search history.

(56) References Cited

U.S. PATENT DOCUMENTS

| | | | |
|---|---|---|---|
| 4,811,308 A * | 3/1989 | Michel | 367/136 |
| 5,410,519 A | 4/1995 | Hall et al. | |
| 5,721,712 A * | 2/1998 | LaPointe | 367/136 |
| 6,178,141 B1 * | 1/2001 | Duckworth et al. | 367/127 |
| 7,372,773 B2 | 5/2008 | Horak | |
| 7,606,115 B1 * | 10/2009 | Cline et al. | 367/136 |
| 2006/0227664 A1 * | 10/2006 | Horak | 367/136 |
| 2009/0257314 A1 * | 10/2009 | Davis et al. | 367/125 |
| 2010/0284249 A1 * | 11/2010 | Steadman | 367/118 |

OTHER PUBLICATIONS

Ferguson et al., "Turboprop and rotary wing aircraft flight parameter estimation using both narrow-band and broadband passive acoustic signal-processing methods", J. Acoust.soc. Am. 108(4), Oct. 2000, pp. 1763-1771.
"Thales", The Museum of Air Traffic Control, 2007, retrieved Mar. 31, 2009 http://www.atcmuseum.org/vendors/thales_overview.asp.
U.S. Appl. No. 12/102,272, filed Apr. 14, 2008, Davis.

* cited by examiner

*Primary Examiner* — Daniel Pihulic
(74) *Attorney, Agent, or Firm* — Yee & Associates, P.C.

(57) ABSTRACT

The different advantageous embodiments provide a method and apparatus for detecting an aircraft. The different advantageous embodiments may provide a method for detecting an acoustic emission emitted by the aircraft using a number of acoustic sensors to form a detected acoustic emission. The aircraft may be identified from the detected acoustic emission to form an identified aircraft. A bearing may be estimated for the identified aircraft using the detected acoustic emission.

15 Claims, 10 Drawing Sheets

ACOUSTIC AIRPORT SURVEILLANCE SYSTEM

BACKGROUND INFORMATION

1. Field

The present disclosure relates generally to monitoring systems and in particular to a method and apparatus for surveillance of aircraft in an airport environment. Still more particularly, the present disclosure relates to a method and apparatus for detecting, tracking and classifying aircraft using sound sensors distributed across a surveillance area.

2. Background

An ability to detect and track aircraft in an airport environment is an important capability for areas where ground surveillance radars do not exist or are limited in detection scope. Today, air traffic control radar systems are used to attempt to track and identify aircraft moving within an airport environment, such as on a runway or taxiway. These radar systems may only be implemented in large airports due to the high cost of these systems.

While these systems may provide detection of moving aircraft within an airport environment, some airports may have sensing gaps where the aircraft operating on a runway or taxiway may go undetected. In addition, these sensing systems require the aircraft to actually move before they can detect and alert human air traffic controllers of potential runway incursions. This gives controllers mere seconds to respond to a detected movement that may pose a potential runway conflict. This type of sensing system offers limited capabilities that provide a small amount of time for air traffic controllers to respond. Additionally, many airport environments may not possess the resources to acquire and implement expensive radar systems, and must rely on visual detection by human air traffic controllers.

Therefore, it would be advantageous to have a method and apparatus that takes into account one or more of the issues discussed above as well as possible other issues.

SUMMARY

The different advantageous embodiments provide a method, apparatus, and computer program product for detecting an aircraft. The different advantageous embodiments may provide a method for detecting an acoustic emission emitted by the aircraft using a number of acoustic sensors to form a detected acoustic emission. The aircraft may be identified from the detected acoustic emission to form an identified aircraft. A bearing may be estimated for the identified aircraft using the detected acoustic emission.

In one advantageous embodiment, a method is provided for detecting an aircraft operating in an airport environment. An acoustic emission is detected using a number of acoustic sensors. A signature from the acoustic emission is identified to form an identified signature. A source of the acoustic emission is identified using the identified signature to form an identified source. A bearing is estimated for the identified source of the acoustic emission to form an estimated bearing. A message is generated based on the identified signature and the estimated bearing for the source of the acoustic emission.

In another advantageous embodiment, an apparatus comprises a number of acoustic sensors and a data processing system. The number of acoustic sensors is capable of detecting an acoustic emission from an aircraft. The data processing system is in communication with the number of acoustic sensors and is capable of monitoring for the acoustic emission from the aircraft and estimating a bearing of the aircraft using acoustic data for the acoustic emission.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
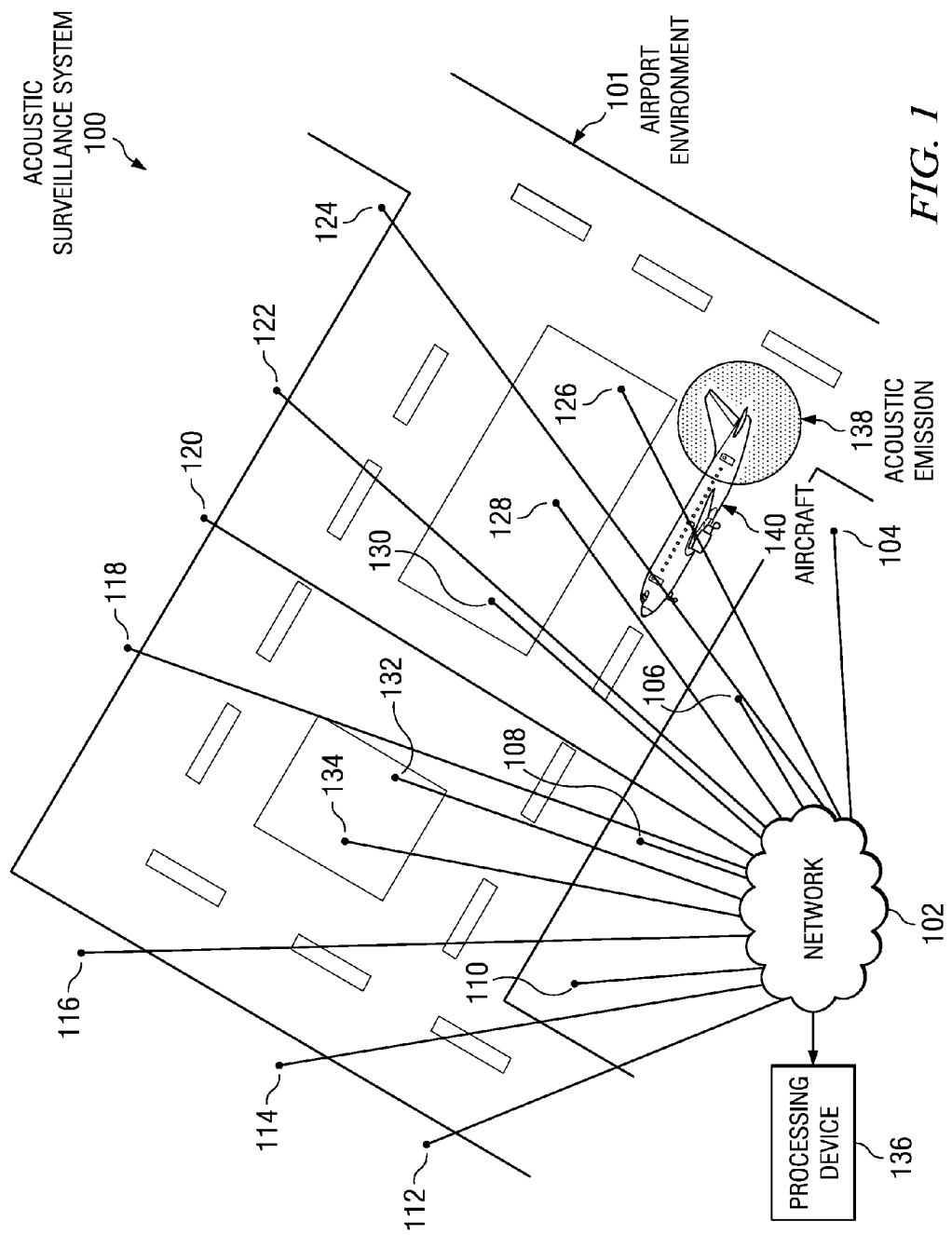
FIG. 1 is an illustration of an acoustic surveillance system in which an advantageous embodiment may be implemented.

With reference now to the figures and in particular with reference to FIG. 1, an illustration of an acoustic surveillance system is depicted in accordance with an advantageous embodiment. Acoustic surveillance system 100 may be implemented in a number of different environments. In this illustrative example, acoustic surveillance system 100 is implemented in airport environment 101. Acoustic surveillance system 100 may be used to detect a vehicle in an environment, such as airport environment 101. A vehicle may be, without limitation, an aircraft. An aircraft may include, for example, without limitation, an airplane, helicopter, unmanned aerial vehicle, and/or other air vehicles.

Acoustic surveillance system 100 may be implemented in a network environment including network 102. In these illustrative examples, network 102 may include a number of different media for transmitting data to processing device 136. This media may include, for example, the internet, wireless transmissions, fiber optic lines, pipeline communication networks, and other wired or wireless medium. Further, network 102 may be, for example, a single network or a combination of different networks. Network 102 may include traditional types of networks, such as, for example, local area networks, wide area networks, the Internet, or other types of networks.

Additionally, network 102 may be implemented using networks based on existing communication lines, such as, for example, telephone lines and/or commercial fiber optics networks. In other advantageous embodiments, network 102 also may employ wireless networks and satellite networks. In other advantageous embodiments, network 102 may transmit information through other media, such as power lines or other suitable media. Network 102 may employ one type of transmission media or multiple types of transmission media depending on the particular implementation.

In this example, acoustic surveillance system 100 includes sensors 104, 106, 108, 110, 112, 114, 116, 118, 120, 122, 124, 126, 128, 130, 132, and 134. Additionally, acoustic surveillance system 100 also includes processing device 136 that collects and processes the data from the sensors.

These sensors may be, for example, acoustic sensors. One or more of these sensors may detect acoustic emission 138 generated by aircraft 140. Acoustic emission 138 is the sound that aircraft 140 generates. From acoustic emission 138, a signature may be identified. Aircraft 140 may generate frequencies within acoustic emission 138 that allow for the identification of aircraft 140. In these examples, acoustic emission 138 is the sound that aircraft 140 generates during initialization, or power-up, of one or more engines and/or propellers associated with aircraft 140. The sound may be a result of different levels of exhaust, compressor or propeller tonals associated with one or more engines at a certain level of power-up. The sounds may also be the result of propeller rotations associated with an aircraft with propellers. Acoustic surveillance system 100 may be capable of identifying the presence of interfering sources of noise, such as ground vehicles and airport personnel, and distinguishing between the interfering noise and the engine and/or propeller sounds.

Acoustic surveillance system 100 may identify a location for aircraft 140 using acoustic emission 138. Acoustic surveillance system 100 may also identify a bearing for aircraft 140 using acoustic emission 138.

Sensors 104, 106, 108, 110, 112, 114, 116, 118, 120, 122, 124, 126, 128, 130, 132, and 134 may be distributed across a geographic area. These sensors may be located on various natural and manmade features. For example, these sensors may be located on platforms, such as, for example, without limitation, air traffic control towers, aircraft hangers, maintenance hangers, terminal buildings, and other suitable features. In another example, these sensors may be located on natural features of a geographic area, such as, for example, without limitation, ground cover, trees, and other suitable features. In the illustrative example of airport environment 101, these sensors may be located along the path of a runway, taxiway, and other suitable features of an airport environment. The data generated by these sensors may be sent to processing device 136 through network 102.

Acoustic surveillance system 100 may be able to detect acoustic emissions of an aircraft during engine initiation, or power-up, of the aircraft before aircraft movement is detectable by radar systems. In these advantageous embodiments, detecting refers to detecting the presence of an aircraft and/or tracking the aircraft movement. Acoustic surveillance system 100 may detect the presence of an aircraft, even predict its next action based on the acoustic emissions of the aircraft, and track the aircraft upon commencement of its next action. In these advantageous embodiments, acoustic surveillance system 100 may provide coverage for areas in which radar is present yet ineffective prior to aircraft movement, or for areas without radar coverage. Acoustic surveillance system 100 may provide an ability to detect aircraft before an aircraft begins to move, and track the bearing of the aircraft once the aircraft initiates movement.

Further, acoustic surveillance system 100 may be implemented using low cost sensing, processing and communications components to assemble an area surveillance system of lower total cost than the total cost of radar systems designed to cover the same area. With this type of acoustic system, in addition to detecting and tracking aircraft, acoustic emission 138 may provide information needed to identify a type of aircraft as well as other attributes about the aircraft.

The illustration of acoustic surveillance system 100 is provided for purposes of depicting one manner in which different advantageous embodiments may be implemented. This illustration is not meant to imply architectural limitations as how acoustic surveillance system 100 may be implemented. For example, multiple processing devices may be used to collect and process very widely spaced or distributed sensors 104, 106, 108, 110, 112, 114, 116, 118, 120, 122, 124, 126, 128, 130, 132, and 134 in FIG. 1. Additionally, acoustic surveillance system 100 in FIG. 1 may complement other detection systems to provide identification of movement for aircraft.

As another example, other numbers of acoustic sensors and other arrangements of acoustic sensors may be employed. For example, in some advantageous embodiments, only four acoustic sensors may be employed, while fifty acoustic sensors may be employed in others. Further, these acoustic sensors may be arranged at different spacing or distances away from each other, depending upon acoustic propagation characteristics of differing terrain situations. Further, the different acoustic sensors illustrated may be of the same type or different types of acoustic sensors.

The different advantageous embodiments recognize and take into account that current systems for ground surveillance and tracking aircraft at airports may only detect airplane movements when the aircraft begins moving. Current air traffic control radar systems are used to attempt to track and identify aircraft moving within an airport environment, such as on a runway or taxiway. These radar systems may only be implemented in a handful of large airports due to the high cost of these systems.

The different advantageous embodiments recognize and take into account that while these systems may provide detection of moving aircraft within an airport environment, some airports may have sensing gaps where the aircraft operating on a runway or taxiway may go undetected. In addition, these sensing systems may require the aircraft to actually move before they can detect and alert human air traffic controllers of potential runway incursions. This gives air traffic controllers mere seconds to respond to a detected movement that may pose a potential runway conflict. These types of current sensing systems offer limited capabilities that provide a small amount of time for air traffic controllers to respond. Additionally, many airport environments may not possess the resources to acquire and implement expensive radar systems, and must rely on visual detection by human air traffic controllers.

Therefore, the different advantageous embodiments provide a method and apparatus for detecting an aircraft. The different advantageous embodiments may provide a method for detecting an acoustic emission emitted by the aircraft using a number of acoustic sensors to form a detected acoustic emission. The aircraft may be identified from the detected acoustic emission to form an identified aircraft. A bearing may be estimated for the identified aircraft using the detected acoustic emission.

The different advantageous embodiments may further provide a method and apparatus for detecting an aircraft operating in an airport environment. In one advantageous embodiment, a method is provided for detecting an aircraft. An acoustic emission is detected using a number of acoustic sensors. A signature from the acoustic emission is identified to form an identified signature. A source of the acoustic emission is identified using the identified signature to form an identified source. A bearing is estimated for the identified source of the acoustic emission to form an estimated bearing. A message is generated based on the identified signature and the estimated bearing for the source of the acoustic emission.

In another advantageous embodiment, an apparatus comprises a number of acoustic sensors and a data processing system. The number of acoustic sensors is capable of detecting an acoustic emission from an aircraft. The data processing system is in communication with the number of acoustic sensors and is capable of monitoring for the acoustic emission from the aircraft and estimating a bearing of the aircraft using acoustic data for the acoustic emission.

Figure 2:
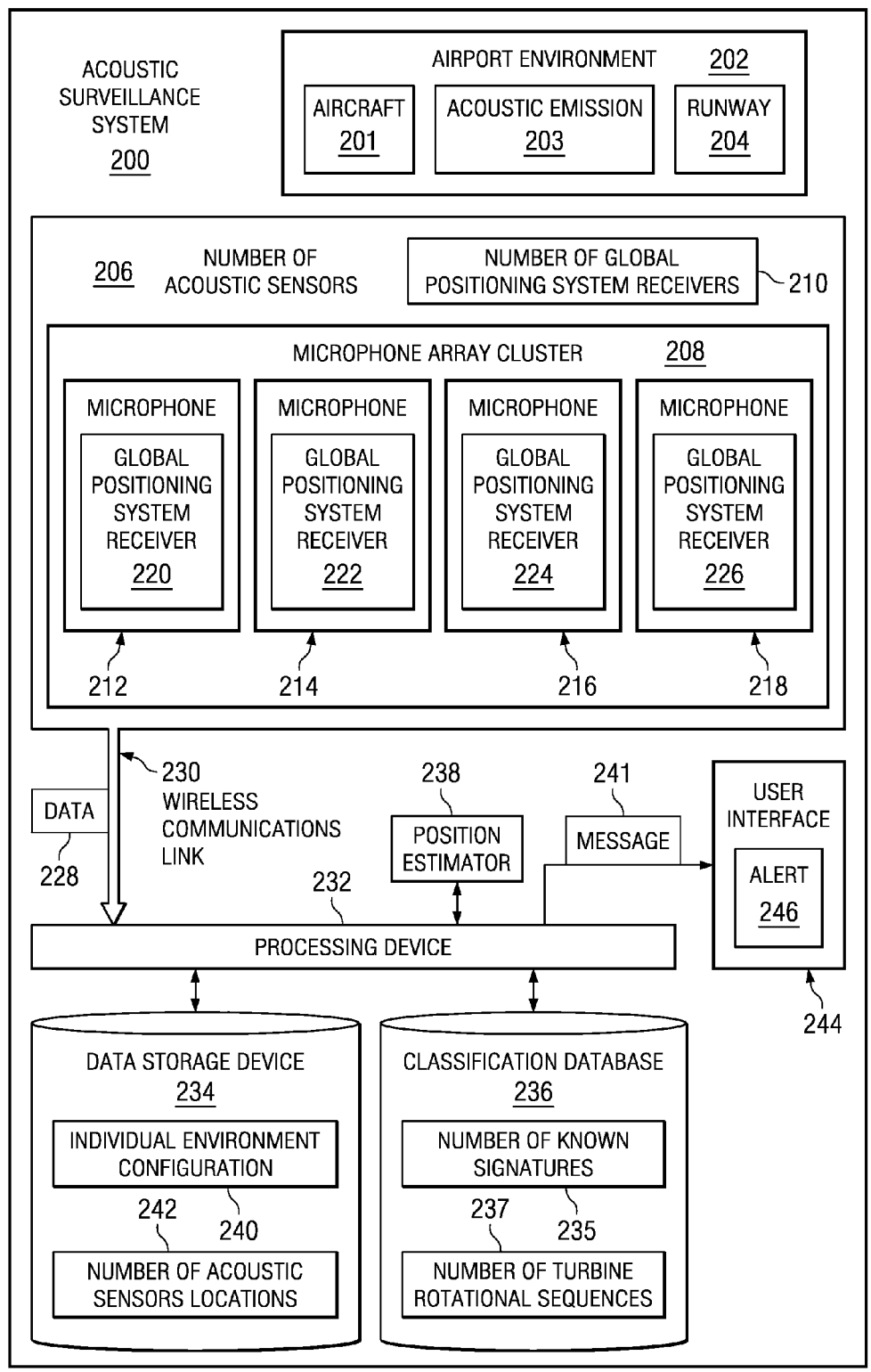
FIG. 2 is a block diagram of an acoustic system in accordance with an advantageous embodiment.

Turning now to FIG. 2, a block diagram of an acoustic surveillance system is depicted in accordance with an advantageous embodiment. In this example, acoustic surveillance system 200 may be implemented in airport environment 202, for example. Airport environment 202 may be an example of one implementation of airport environment 101 in FIG. 1. For example, acoustic surveillance system 200 may be implemented within runway 204 of airport environment 202.

Acoustic surveillance system 200 includes number of acoustic sensors 206. An acoustic sensor may be, for example, without limitation, a microphone. An acoustic sensor may detect sound within a selected range. In an illustrative embodiment, number of acoustic sensors 206 may be an example of one implementation of acoustic sensors 104, 106, 108, 110, 112, 114, 116, 118, 120, 122, 124, 126, 128, 130, 132, and 134 in FIG. 1. Number of acoustic sensors 206 includes number of global positioning system receivers 210. Each acoustic sensor in number of acoustic sensors 206 may be equipped with a global positioning system receiver. In one advantageous embodiment, number of acoustic sensors 206 may be, for example, implemented as microphone array cluster 208. Microphone array cluster 208 may be, for example, a set of omni-directional microphones. As used herein, a set refers to one or more microphones. In one illustrative embodiment, a microphone array cluster may refer to a set of four microphones arranged in a geometric array. In another illustrative embodiment, a microphone array cluster may refer to a set of four or more microphones arranged in a geometric array.

In this illustrative example, microphone cluster array 208 may include microphone 212, microphone 214, microphone 216, and microphone 218. Each of microphones 212, 214, 216, and 218 are equipped with global positioning system receivers 220, 222, 224, and 226, respectively. The global positioning system receivers may provide a time tag or timestamp for data detected by number of acoustic sensors 206, which is included with the acoustic data sent to processing device 232.

Number of acoustic sensors 206 may generate data 228. In an illustrative example, data 228 may include the data for an acoustic emission for an aircraft, as well as possible noise. In these examples, noise is any sound detected that is not generated by an aircraft. Data 228 may also include a timestamp generated by a global positioning system receiver located on the acoustic sensor generating data 228. Number of acoustic sensors 206 may send data 228 over wireless communications link 230 to processing device 232. Data 228 may contain the data generated from detecting sounds, such as acoustic emissions from an aircraft, and a timestamp for the sound detection, for example.

Processing device 232 may provide analog conditioning to separate noise from the desired signal. In these examples, the desired signal is the acoustic emission generated by an aircraft. Further, processing device 232 also may provide analog to digital conversion, as well an ability to generate messages or packets, such as message 241, containing the data analysis for the acoustic emission. This message also may include a time tag or time stamp. The time tag is used for later processing.

Processing device 232 may take various forms. For example, processing device 232 may be an application-specific integrated circuit to perform analog conditioning, analog to digital conversion, and message formation. In other advantageous embodiments, processing device 232 may be a data processing system, such as data processing system 300 in FIG. 3. When processing device 232 is implemented using data processing system 300 in FIG. 3, processing device 232 may perform other types of processing and analysis of information detected by number of acoustic sensors 206. For example, without limitation, this additional processing may include determining whether the data includes an acoustic emission from an aircraft. Additional processing may include, for example, without limitation, removing noise from data 228 to leave only the acoustic emission from the aircraft.

Processing device 232 may access data storage device 234, classification database 236, and position estimator 238 in order to perform additional processing. Data storage device 234 may include, for example, without limitation, individual environment configuration information 240 and number of acoustic sensors locations 242. Individual environment configuration information 240 may contain specific configuration information for each environment in a number of environments in which acoustic system 200 may be implemented. For example, individual environment configuration information 240 may contain specific configuration information for airport environment 202, including the location and configuration of runway 204 within airport environment 202. In this example, airport environment 202 may be a specific airport location with a configuration unique to that location. Number of acoustic sensors locations 242 may contain information about the specific location of each acoustic sensor in a number of acoustic sensors for a corresponding individual environment configuration. In these examples, the information in data storage device 234 is used by processing device 232 to analyze data 228 detected by number of acoustic sensors 206.

Classification database 236 may include, without limitation, number of known signatures 235 and number of turbine rotational frequencies 237. In these examples classification database 236 may be stored on one or more storage devices, attached to processing device 232, and/or distributed across a number of storage devices that may be connected to and/or remote to processing device 232. Number of known signatures 235 may include different acoustic signatures uniquely associated with a number of different types of aircraft. For example, without limitation, a first acoustic signature may be associated with a prop engine aircraft, a second acoustic signature may be associated with a single engine jet, a third acoustic signature may be associated with a twin engine jet, a fourth acoustic signature may be associated with a helicopter, a fifth acoustic signature may be associated with a Cessna 182 aircraft, and so on for a number of different types of aircraft.

Number of turbine rotational frequencies 237 may include information about the different frequency lines in a frequency spectrum related to turbine rotational frequencies that indicate a state of an engine. For example, high frequency lines may indicate the onset of an engine run-up or power-up. In an illustrative example, high frequency lines may be greater than 900 Hz. In another example, low frequency lines and/or a lack of narrowband frequency may indicate that an engine is idling. In an illustrative example, low frequency lines may be less than 900 Hz. Identification of different frequency lines in a spectrum enable estimation and/or identification of vehicle parameters, such as aircraft flight parameters such as speed and slant range for example. Further, a type of vehicle may be identified based on these frequency lines, also known as signatures. For example, a jet aircraft may be identified based on its engine run-up and take-off signature.

Processing device 232 may access classification database 236 in order to compare an identified signature in acoustic emission 203, for example, to the number of known signatures in the database in order to identify the acoustic emission source. For example, without limitation, the identification process may include identifying the acoustic emission as vehicle noise or non-vehicle noise, identifying the acoustic emission as aircraft noise or non-aircraft noise, identifying a type of aircraft, identifying a model of the aircraft type, and/or any other suitable identification of an acoustic emission. Processing device 232 may also use the information from number of turbine rotational frequencies 237 to examine acoustic data 228 and determine the state of aircraft 201. In an illustrative example, the state of aircraft 201 may be engine idling, engine run-up, or aircraft take-off, for example.

When an acoustic emission, such as acoustic emission 203, has been identified as emitted by an aircraft, processing device 232 may then predict potential movement based on the acoustic data, such as data 228, received from number of acoustic sensors 206 detecting the acoustic emission. This prediction may be based on the frequency and/or amplitude levels of the broadband spectrum detected for the acoustic emission. In one illustrative example, a broadband spectrum detected without a narrowband frequency may indicate that the one or more engines for an aircraft, such as aircraft 201, are running at low revolutions per minute, which in turn indicates that the aircraft engines are idling.

In these examples, processing device 232 may predict potential movement and relay information about the potential movement to a user interface. For example, processing device 232 may generate message 241 in order to relay information to user interface 244 and present alert or warning 246 to human air traffic controllers indicating the potential movement. This information can then be used by human air traffic controllers to determine potential runway situations based on the predicted movement of an aircraft, allowing for resolution of these potential situations before actual movement by the aircraft.

Number of acoustic sensors 206 may be placed at a number of locations throughout an environment, such as airport environment 202. In the illustrative example of microphone array cluster 208, during a first time segment microphone 212 may detect one level of amplitude for acoustic emission 203, while microphone 214 and microphone 216 detect another level of amplitude for acoustic emission 203, and microphone 218 detects yet another level of amplitude for acoustic emission 203. During a second subsequent time segment, the amplitude levels detected by each microphone in the array may then shift. Processing device 232 may receive data 228 from microphone array cluster 208 with information about acoustic emission 203 including the different levels of amplitude detected by the individual microphones during the different time segments and the shift from one time segment to the second time segment.

Processing device 232 may use position estimator to process data 228, and in particular the different levels detected and the shift over time. The shift detected by the individual microphones in the array may indicate actual movement by the aircraft. Position estimator 238 may identify a bearing for aircraft 201 based on this information from acoustic emission 203, and track movement of the aircraft based on subsequent acoustic data detected for aircraft 201. The bearing identified for aircraft 201 may be an estimation of a heading for aircraft 201, for example. Identifying multiple shifts over time may be used to track the ground speed of the actual movement of the aircraft. This information may be used to estimate the location and bearing of the aircraft. This information may also be used to predict a potential future location of the aircraft based on the bearing of the aircraft and the predicted movement of the aircraft. For example, based on a bearing of an aircraft heading north towards one end of a runway, and tracking the ground speed of the actual movement of the aircraft, a prediction may be made that the aircraft will reach the north end of the runway at a particular point in time.

Processing device 232 generates message 241 and sends message 241 to user interface 244, which displays information from message 241 as alert 246. An alert may be, for example, without limitation, an indication that an aircraft is powering up, an indication that an aircraft is moving, an indication that an aircraft is moving in a particular direction, and/or any other suitable information. User interface 244 may be implemented by a display device, such as display 314 in FIG. 3, for example. User interface 244 may be located remote from processing device 232, such as at a remote computer or server, for example.

The different components illustrated for acoustic surveillance system 200 in FIG. 2 are not meant to provide architectural limitations to the manner in which different embodiments may be implemented. The different advantageous embodiments may be implemented including components in addition to or in place of those illustrated for acoustic surveillance system 200. Other components shown in FIG. 2 can be varied from the illustrative examples shown. The different embodiments may be implemented using any hardware device or system capable of executing program code. As one example, the processing device may include organic components integrated with inorganic components and/or may be comprised entirely of organic components excluding a human being. For example, a storage device may be comprised of an organic semiconductor.

As another example, position estimator 238 may be located remote from processing device 232, such as in a remote location or remote server accessed over a network, such as network 102 in FIG. 1. In another illustrative example, position estimator 238 may be integrated with processing device 232.

In yet another illustrative example, data storage device 234 may include classification database 236. In still another example, data storage device 234 and classification database 236 may be located at a remote location from processing device 232 and accessed over a wireless network.

Figure 3:
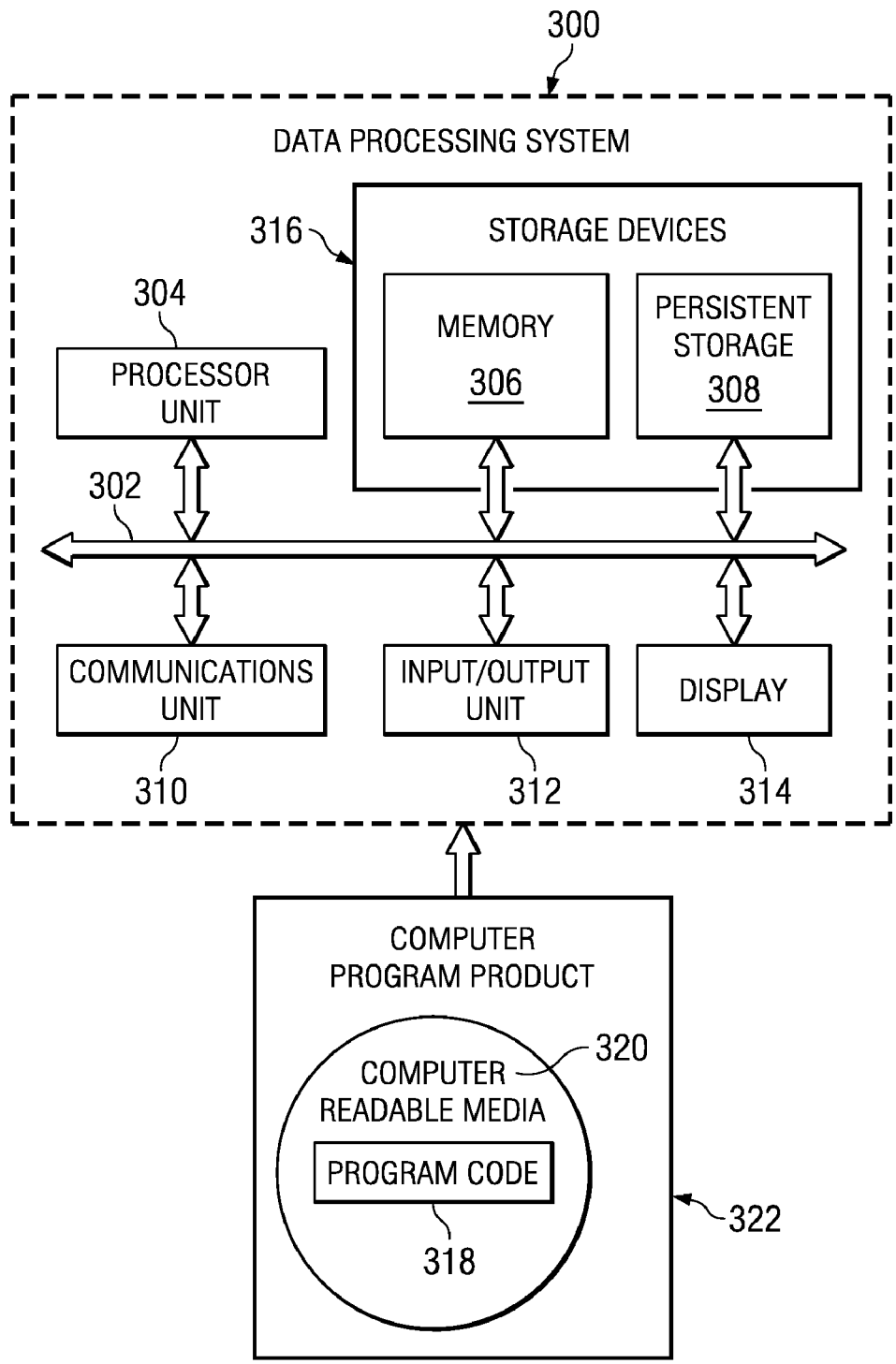
FIG. 3 is a diagram of a data processing system in accordance with an advantageous embodiment.

Turning now to FIG. 3, a diagram of a data processing system is depicted in accordance with an illustrative embodiment. Data processing system 300 is an example of a data processing system that may be used in processing device 232 in FIG. 2 to process data detected by acoustic sensors 104, 106, 108, 110, 112, 114, 116, 118, 120, 122, 124, 126, 128, 130, 132, and 134 in FIG. 1.

In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices 316. A storage device is any piece of hardware that is capable of storing information, such as, for example without limitation, data, program code in functional form, and/or other suitable information either on a temporary basis and/or a permanent basis. Memory 306, in these examples, may be, for example, a random access memory or any other suitable volatile or non-volatile storage device. Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user. Display 314 may be an example of one implementation of user interface 244 in FIG. 2.

Instructions for the operating system, applications and/or programs may be located in storage device 316, which are in communication with processor unit 304 through communications fabric 302. In these illustrative examples the instruction are in a functional form on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 318 is located in a functional form on computer readable media 320 that is selectively removable and may be loaded onto or transferred to data processing system 300 for execution by processor unit 304. Program code 318 and computer readable media 320 form computer program product 322 in these examples. In one example, computer readable media 320 may be in a tangible form, such as, for example, an optical or magnetic disc that is inserted or placed into a drive or other device that is part of persistent storage 308 for transfer onto a storage device, such as a hard drive that is part of persistent storage 308. In a tangible form, computer readable media 320 also may take the form of a persistent storage, such as a hard drive, a thumb drive, or a flash memory that is connected to data processing system 300. The tangible form of computer readable media 320 is also referred to as computer recordable storage media. In some instances, computer readable media 320 may not be removable.

Alternatively, program code 318 may be transferred to data processing system 300 from computer readable media 320 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

In some illustrative embodiments, program code 318 may be downloaded over a network to persistent storage 308 from another device or data processing system for use within data processing system 300. For instance, program code stored in a computer readable storage medium in a server data processing system may be downloaded over a network from the server to data processing system 300. The data processing system providing program code 318 may be a server computer, a client computer, or some other device capable of storing and transmitting program code 318.

The different components illustrated for data processing system 300 are not meant to provide architectural limitations to the manner in which different embodiments may be implemented. The different advantageous embodiments may be implemented in a data processing system including components in addition to or in place of those illustrated for data processing system 300. Other components shown in FIG. 3 can be varied from the illustrative examples shown. The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 300 is any hardware apparatus that may store data. Memory 306, persistent storage 308 and computer readable media 318 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 306 or a cache such as found in an interface and memory controller hub that may be present in communications fabric 302.

Figure 4:
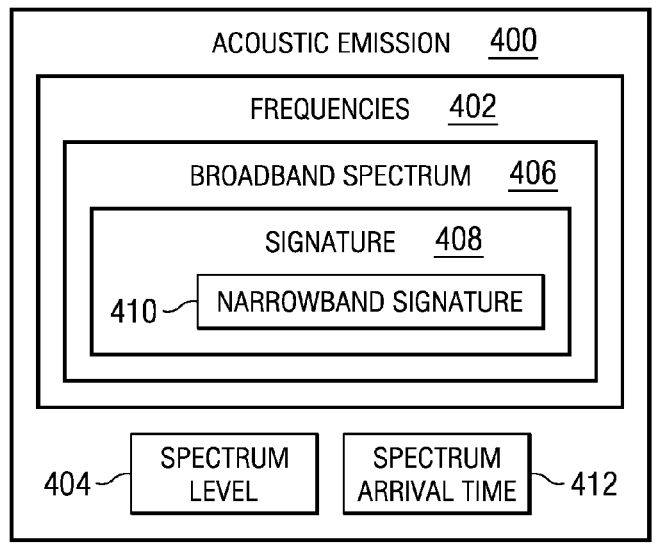
FIG. 4 is a diagram illustrating an acoustic emission in accordance with an advantageous embodiment.

With reference now to FIG. 4, a diagram illustrating an acoustic emission is depicted in accordance with an advantageous embodiment. In this example, acoustic emission 400 is the sound generated by an aircraft. Acoustic emission 400 may be an example of acoustic emission 138 in FIG. 1 and/or acoustic emission 203 in FIG. 2.

Acoustic emission 400 may include frequencies 402 and spectrum level 404. Frequencies 402 are the different frequencies contained in the sound generated by the aircraft that forms acoustic emission 400. Spectrum level 404 is the amplitude of frequencies 402. Spectrum level 404 may include amplitude for each frequency. In other words, spectrum level 404 is the "loudness" of acoustic emission 400.

Frequencies 402 in acoustic emission 400 form broadband spectrum 406. Broadband spectrum 406 is the entire range of frequencies contained in acoustic emission 400. A broadband spectrum is the total bandwidth of sound frequencies detected by a detection system in these examples. For example, broadband spectrum 406 is the portion of frequencies 402 detected by a microphone or other type of acoustic sensor. A broadband spectrum may be, for example, tens to hundredths of Hertz. In other words, broadband spectrum 406 may be only a portion of frequencies 402 for acoustic emission 400.

Signature 408 contains frequencies within broadband spectrum 406 that may be used to identify an aircraft from acoustic emission 400. In some advantageous embodiments, signature 408 may encompass all frequencies within broadband spectrum 406. In the illustrative embodiments, signature 408 may be a subset of broadband spectrum 406. In these examples, this subset also is narrowband signature 410.

Narrowband signature 410 is a selected number or subset of frequencies from broadband spectrum 406. For example, narrowband signature 410 may be the frequencies identified for the propeller(s) and/or exhaust of the aircraft generating acoustic emission 400. This narrowband signature may be used to classify or identify various parameters about the aircraft generating acoustic emission 400. For example, narrowband signature 410 may be compared to a stored signature in a classification database, such as classification database 236 in FIG. 2.

In these examples, the narrowband spectrum in narrowband signature 410 may be used to classify the aircraft. The narrowband spectrum is a subset of the total bandwidth of the acoustic system. Within a narrowband spectrum, each band is a subdivision containing a portion of the spectrum. For example, a narrowband may have a width of one Hertz or less. In other words, a band within the narrowband spectrum may be analogous to a musical note, while a broadband spectrum may comprise multiple contiguous musical notes. The narrowband spectrum is a subset of the total bandwidth that is present, and the subset may or may not be contiguous frequencies.

In these examples, narrowband signature 410 may be a shifted and/or un-shifted set of frequencies within broadband spectrum 406. These signatures may be shifted because of a Doppler effect. This effect results in a change in frequency as perceived by the acoustic sensor when the aircraft moves relative to the location of the acoustic sensor. The received frequency increases as the aircraft moves toward the acoustic sensor and decreases when the aircraft moves away from the acoustic sensor. At the instant when the aircraft is at the closest point of approach to an acoustic sensor, the relative aircraft velocity is zero and the acoustic frequencies received at the acoustic sensor have zero Doppler shift. The closest point of approach, in these examples, is the minimum distance that occurs between the aircraft and the acoustic sensor. Frequencies with zero Doppler shift are alternately termed as un-shifted frequencies.

Thus, when the aircraft is at the closest point of approach to an acoustic sensor, narrowband signature frequencies 410 received by the acoustic sensor are identical to the narrowband signature frequencies radiated by the aircraft. These observed zero Doppler or un-shifted frequencies provide a common acoustic characterization of the aircraft that may be associated with that aircraft at every acoustic sensor in the system.

In the example of an array cluster of acoustic sensors, such as microphone array cluster 208 in FIG. 2, narrowband frequencies may be shifted when the aircraft moves relative to the location of the array cluster of acoustic sensors. The received frequency increases as the aircraft moves toward a first acoustic sensor in the array cluster and decreases when the aircraft moves away from the first acoustic sensor in the array cluster. At the instant when the aircraft is at the closest point of approach to the first acoustic sensor in the array cluster, the relative aircraft velocity is zero and the acoustic frequencies received at the first acoustic sensor have zero Doppler shift. Bearing and elevation angles to the aircraft may be calculated at any time that the aircraft is detected by a number of acoustic sensors, such as microphone array cluster 208 in FIG. 2, not just at the closest point of approach. A microphone array cluster, for the purpose of measuring bearing and elevation angles, consists of at least four closely spaced microphones, such as 212, 214, 216 and 218 of microphone array cluster 208 in FIG. 2. Bearing and elevation angles are calculated by a processing device, such as processing device 232 in FIG. 2. This calculation is performed by measuring the differences of spectrum arrival times 412 across the microphone array cluster of either broadband spectrum 406 or narrowband signature 410.

The different components illustrated for acoustic emission 400 are not meant to provide architectural limitations to the manner in which different embodiments may be implemented. The different advantageous embodiments may be implemented including components in addition to or in place of those illustrated for acoustic emission 400. Other components shown in FIG. 4 can be varied from the illustrative examples shown.

Figure 5:
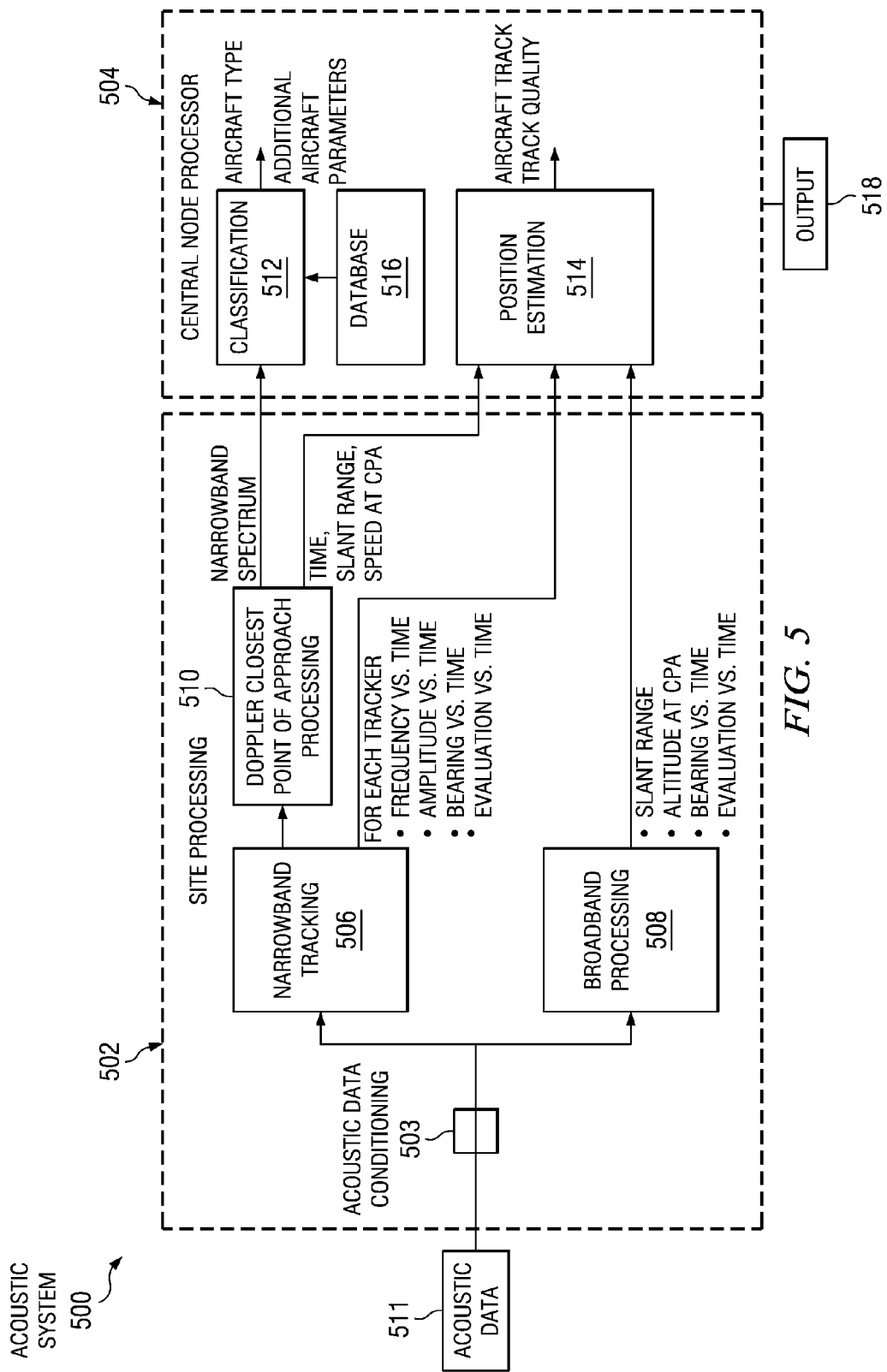
FIG. 5 is a block diagram of functional components used to detect an aircraft in accordance with an advantageous embodiment.

With reference now to FIG. 5 a block diagram of functional components used to detect and track an aircraft is depicted in accordance with an advantageous embodiment. In this depicted example, acoustic system 500 is an example of functional components that may be implemented in acoustic surveillance system 100 in FIG. 1. In these illustrative examples, the different functional components include site processing 502 and central node processor 504. Site processing 502 processes data from an acoustic sensor. As illustrated, site processing 502 comprises acoustic data conditioning 503, narrowband tracking 506, broadband processing 508, and Doppler closest point of approach processing 510. This type of processing may be performed at a central node, such as processing device 136 in FIG. 1, or processing device 232 in FIG. 2. Alternatively, this type of processing may be performed at different acoustic sensors with the results being transmitted to processing device 136 in FIG. 1.

Identification processes may also be implemented in the processing device. Both processing device 136 in FIG. 1 and central node processor 504 include classification 512 and position estimation 514. These processes are used to identify aircraft from acoustic emissions that may be received in acoustic data 511. In these examples, acoustic data 511 is in an analog form. This classification may occur in different ways. The classification may occur once, for example, without limitation, the first time acoustic data 511 is received for an aircraft. In other advantageous embodiments, the classification may be performed sequentially. In other words, classification 512 may classify the aircraft each time an acoustic sensor detects an acoustic emission and sends acoustic data 511.

In operation, site processing 502 receives acoustic data 511 from an acoustic sensor. Acoustic data 511 contains an acoustic emission, such as acoustic emission 138 in FIG. 1, and/or acoustic emission 400 in FIG. 4. Analog acoustic data 511 is converted to digital data by acoustic data conditioning 503 and is then processed by narrowband tracking 506 and broadband processing 508.

Narrowband tracking 506 processes the narrowband portion of the acoustic emission in acoustic data 511. This narrowband portion may be, for example, narrowband signature 410 in FIG. 4. This component identifies the narrowband signature for the acoustic emission in these examples. The signature may be shifted and unshifted, depending on where the acoustic emission was detected. Narrowband tracking 506 processes acoustic data 511 by assigning a frequency tracker to each discernable frequency line.

In these examples, a Fast Fourier Transform (FFT) is performed on acoustic data 511. Thus, the aircraft emission is decomposed into its spectral components. A detection of an aircraft is declared or indicated if the magnitude of a Fast Fourier Transform frequency bin is larger by some factor than the adjacent bins. The adjacent bins are assumed to contain only noise, in these illustrative examples. A Kalman filter may be assigned to this frequency bin. The Kalman filter is the frequency tracker in these examples.

Thus, as long as sufficient signal-to-noise ratio is present, the Kalman filter follows changes in frequency due to changes in the geometry between the aircraft and the acoustic sensor. A Kalman filter is assigned to each component of the narrowband spectrum of the aircraft. Thus, narrowband tracking identifies the frequencies in the acoustic emission. In these examples, a "frequency line" refers to a "frequency component" of the narrowband signature.

Narrowband tracking 506 generates data associated with trackers. Each tracker is associated with a frequency versus time and amplitude versus time. In other words, each frequency and amplitude is associated with a particular time. This time may be obtained from time stamps located in acoustic data 511. In an advantageous embodiment, the time stamps may be generated by a global positioning system receiver associated with the acoustic sensor, such as global positioning system receiver 220 associated with microphone 212 in FIG. 2, for example. This output is sent to Doppler closest point of approach processing 510 and position estimation 514. If acoustic data 511 is from a microphone array, narrowband tracking 506 and broadband processing 508 each process acoustic data 511 to provide bearing and elevation angles for an aircraft at any time that the aircraft is detected by a microphone array, such as microphone array cluster 208 in FIG. 2 for example. This information is sent to position estimation 514.

In these examples, Doppler closest point of approach processing 510 may also process the output from narrowband tracking 506 using the set of time-frequency points that correspond to the change in frequency from high-Doppler to low-Doppler. In these examples, a high-Doppler indicates that the aircraft is approaching the sensor. A low-Doppler indicates that the aircraft is flying away from the sensor. This set of time-frequency points is provided by the Kalman filter tracker assigned by narrowband tracking 506 in these examples. By examining the shape of the time-frequency curve through closest point of approach, Doppler closest point of approach processing 510 provides estimates of time at the closest point of approach, as well as slant range and speed.

Doppler closest point of approach processing 510 generates a narrowband spectrum, which is sent to classification 512. This narrowband spectrum may be a narrowband signature for the detected aircraft.

Further, Doppler closest point of approach processing 510 also generates time, slant range, and speed at the closest point of approach. In these examples, the closest point of approach is the point at which the aircraft is closest to the acoustic sensor in these examples. This information is sent to position estimation 514.

Classification 512 may receive this data for a set of one or more acoustic sensors to identify the aircraft type, as well as other aircraft parameters. These other parameters include, for example, a type of engine in the aircraft, a number of blades in a propeller, a number of propellers, whether the aircraft is a fixed wing aircraft, whether the aircraft is a helicopter, a number of engines in the aircraft, and other suitable parameters. In these examples, classification 512 may identify these parameters using database 516. Database 516, may be, for example, a database of narrowband signatures for known aircraft, such as classification database 236 in FIG. 2 for example.

Position estimation 514 receives the processed information for a set of acoustic sensors. This information may be used to estimate the location of the aircraft. The size of the area of uncertainty may vary depending on the number of acoustic sensors from which data is received. For example, the area of uncertainty is greater when acoustic data 511 is received from a single sensor as opposed to when acoustic data 511 is received from four acoustic sensors.

In these advantageous embodiments, it is desirable to receive data from at least four acoustic sensors for performing estimation of positions. Position estimation 514 may output aircraft track quality. In the illustrative examples, aircraft track quality is a measure of the area of uncertainty in the estimated aircraft position at a given time.

The position and tracking data is then provided as output 518 to a user interface connected to the network for access by air traffic controllers.

The different components illustrated for acoustic system 500 are not meant to provide architectural limitations to the manner in which different embodiments may be implemented. The different advantageous embodiments may be implemented including components in addition to or in place of those illustrated for acoustic system 500. Other components shown in FIG. 5 can be varied from the illustrative examples shown.

With reference now to FIGS. 6-9, diagrams illustrating the detection and tracking of an aircraft are depicted in accordance with an advantageous embodiment.

Figure 6:
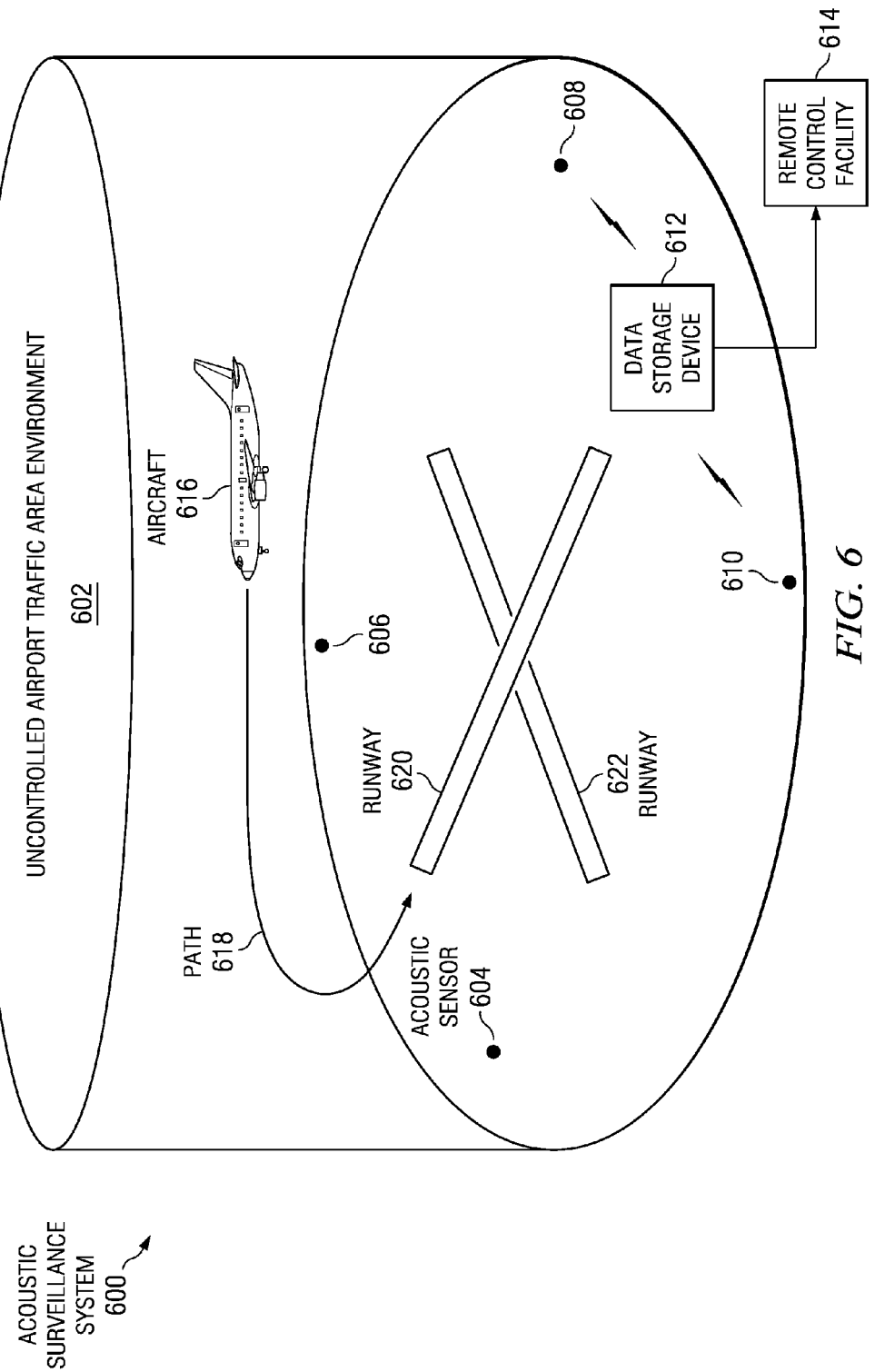
FIGS. 6-9 are diagrams illustrating the detection of an aircraft in an airport environment in accordance with an advantageous embodiment.

In FIG. 6, a diagram illustrating an acoustic surveillance system implemented in an uncontrolled airport traffic area environment is depicted in accordance with an advantageous embodiment. Acoustic surveillance system 600 may be an example of one implementation of acoustic surveillance system 200 in FIG. 2. Uncontrolled airport traffic area environment 602 may be an illustrative example of an uncontrolled airport traffic area, such as, without limitation, an airport without traffic control towers, an airport without human traffic controllers, and any other suitable uncontrolled airport traffic area.

In one advantageous embodiment, acoustic sensors 604, 606, 608, and 610 are distributed across uncontrolled airport traffic area environment 602. Acoustic sensors 604, 606, 608, and 610 may be an illustrative example of one implementation of number of acoustic sensors 206 in FIG. 2. Acoustic sensors 604, 606, 608, and 610 may be implemented as microphone array clusters, such as microphone array cluster 208 in FIG. 2, in one illustrative example. Acoustic surveillance system 600 may provide data on in-flight aircraft movements detected in the vicinity of uncontrolled airport traffic area environment 602. The data may be stored locally on data storage device 612 of acoustic surveillance system 600. The data may also be transmitted by acoustic surveillance system 600 to remote control facility 614.

In an illustrative example, aircraft 616 may be detected by one or more of acoustic sensors 604, 606, 608, and 610 in uncontrolled airport traffic area environment 602. The acoustic data detected acoustic sensors 604, 606, 608, and 610 may be processed by acoustic surveillance system 600 and may be transmitted to remote control facility 614. The data provided by acoustic surveillance system 600 as a result of the acoustic data detected by acoustic sensors 604, 606, 608, and 610 may indicate that aircraft 616 is on path 618. Path 618 may correspond to a landing pattern consistent with aircraft 616 landing on runway 620 as opposed to runway 622. This data may be used by air traffic controllers at remote control facility 614 to predict potential runway situations for uncontrolled airport traffic area environment 602 despite the fact that the air traffic controllers are not physically present at uncontrolled airport traffic area environment 602. This may provide low-cost surveillance coverage for many airports where no control towers or other sensing systems exist.

Figure 7:
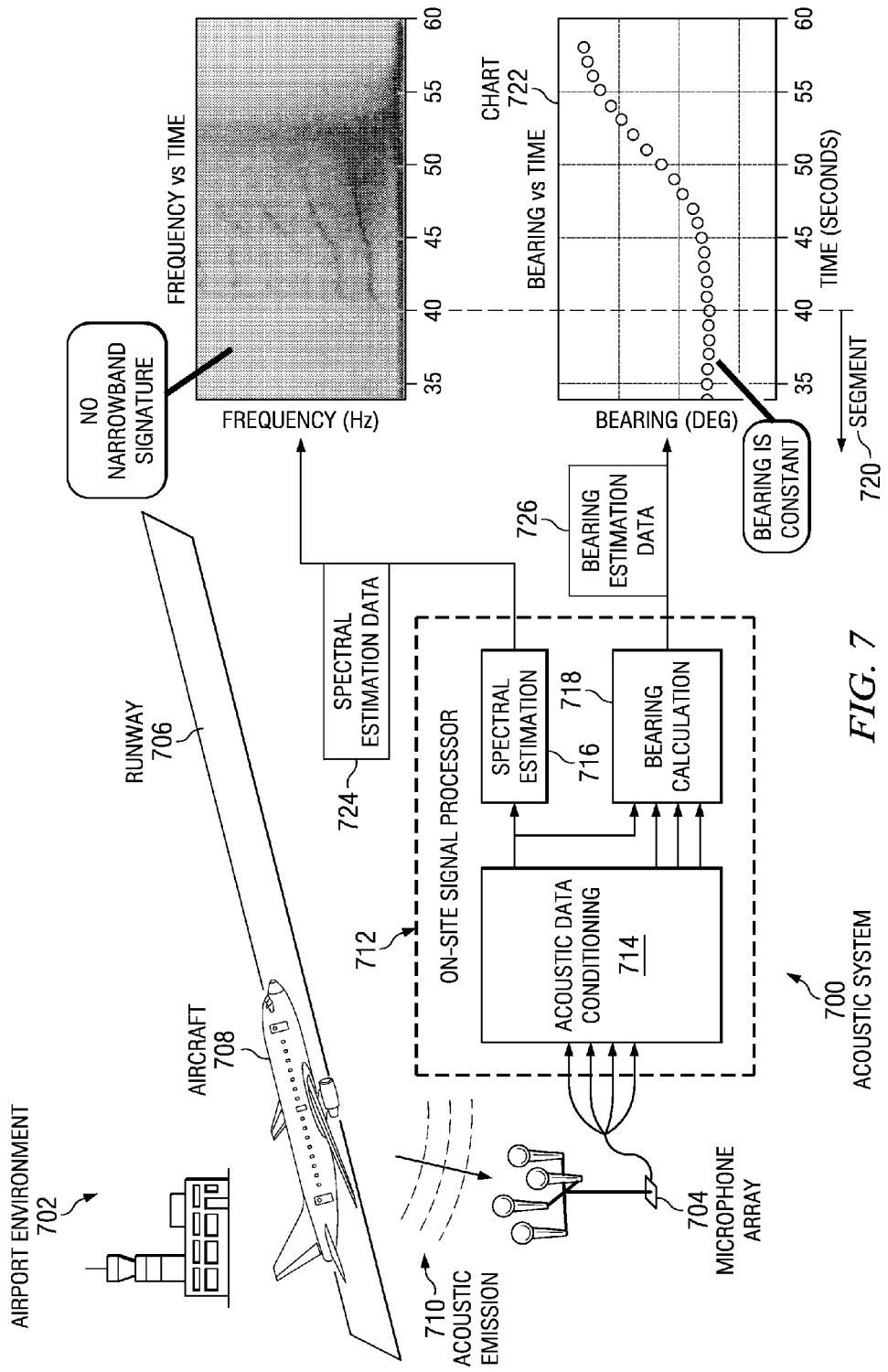

With reference now to FIG. 7, a diagram illustrating the detection of an aircraft prior to engine run-up is depicted in accordance with an advantageous embodiment. Acoustic system 700 may be an example of one implementation of acoustic surveillance system 200 in FIG. 2. In this illustrative example, acoustic system 700 is implemented in airport environment 702.

In one advantageous embodiment, acoustic system 700 may include microphone array 704. Microphone array 704 may be an example of one implementation of number of acoustic sensors 206 in FIG. 2, such as the illustrative example of microphone array cluster 208 in FIG. 2. Microphone array 704 may be located near runway 706 in airport environment 702. Aircraft 708 may be located at one end of runway 706. In another illustrative example, aircraft 708 may be located at any portion of runway 706. In this illustrative example, aircraft 708 is stationary and the engines are at low revolutions per minute, emitting acoustic emission 710.

Microphone array 704 detects the broadband spectrum of acoustic emission 710, which contains the entire range of frequencies contained in acoustic emission 710. On-site signal processor 712 receives the acoustic data from microphone array 704 including the broadband spectrum information for acoustic emission 710. On-site signal processor 712 is an example of one implementation of site processing 502 in FIG. 5. In this illustrative example, signal processing is performed at microphone array 704 with the results being transmitted to a processing device, such as processing device 232 in FIG. 2, or central node processor 504 in FIG. 5, for example. In another advantageous embodiment, this signal processing may be performed at a central node, such as processing device 232 in FIG. 2, or central node processor 504 in FIG. 5, for example.

The acoustic data for acoustic emission 710 is received by on-site signal processor 712 and undergoes acoustic data conditioning 714. Acoustic data conditioning 714 is an example of one implementation of the processing that occurs by acoustic data conditioning 503 in FIG. 5. Spectral estimation 716 may process the narrowband portion and broadband spectrum of acoustic emission 710, and produce spectral estimation data 724. Bearing calculation 718 may process the narrowband portion and broadband spectrum of acoustic emission 710, and produce bearing estimation data 726. In this illustrative example, no narrowband frequency lines are detected for acoustic emission 710. As a result, spectral estimation 716 determines that the engines are at low revolutions per minute. In this illustrative example, acoustic data conditioning 714 may also determine that spectrum arrival time for the acoustic data received is constant. As a result, bearing calculation 718 determines that the bearing for aircraft 708 is constant. In other words, the aircraft is stationary and the engines are not being run up.

This processing of acoustic data for acoustic emission 710 may be done during time segment 720. Segment 720 represents a segment of time prior to the forty second mark depicted in bearing versus time chart 722. This detection occurs while aircraft 708 is stationary and does not require movement from aircraft 708 in order to determine bearing.

The different components illustrated for acoustic system 700 are not meant to provide architectural limitations to the manner in which different embodiments may be implemented. The different advantageous embodiments may be implemented including components in addition to or in place of those illustrated for acoustic system 700. Other components shown in FIG. 7 can be varied from the illustrative examples shown.

Figure 8:
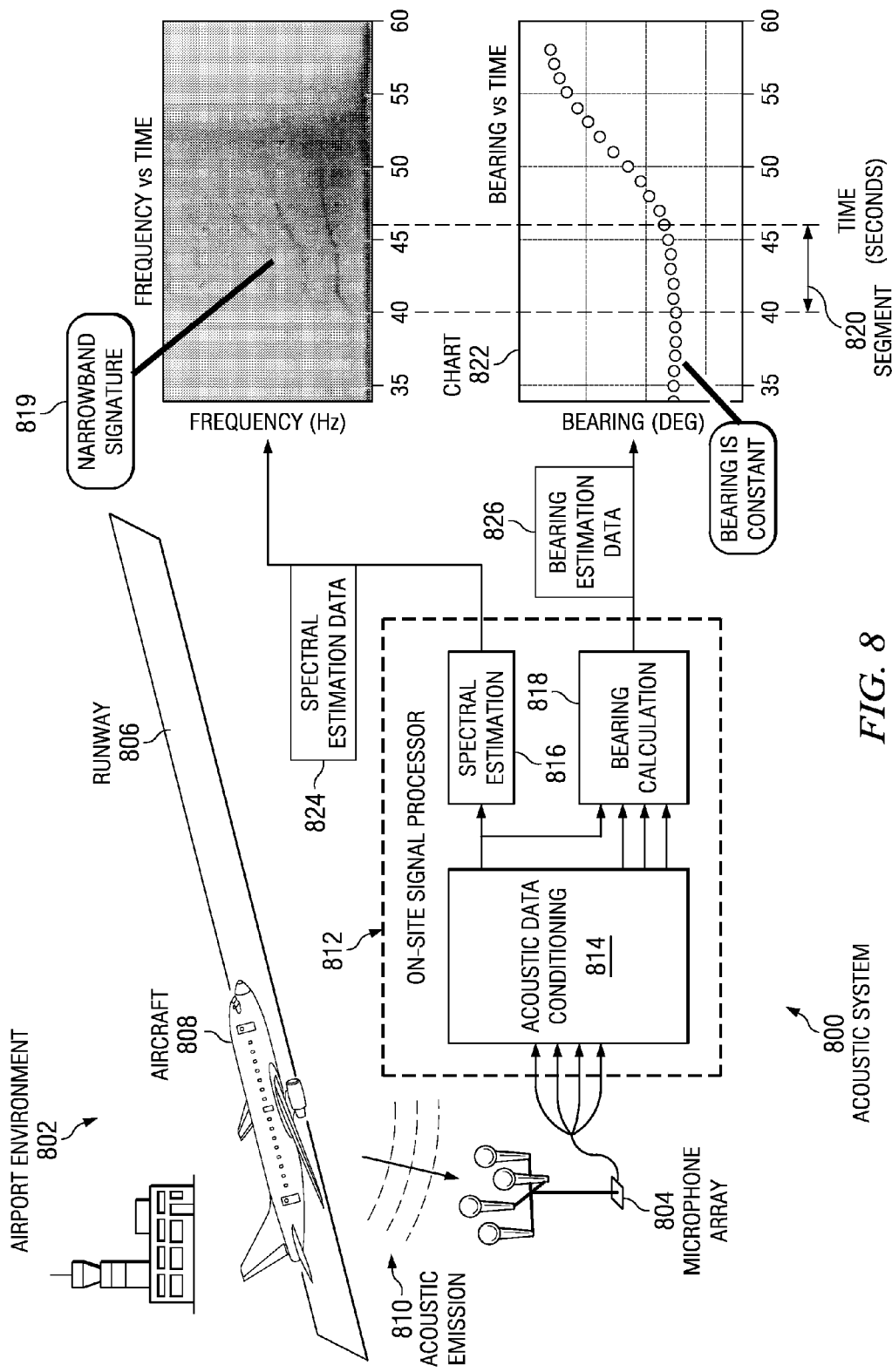

With reference now to FIG. 8, a diagram illustrating the detection of an aircraft at the start of engine run-up is depicted in accordance with an advantageous embodiment. Acoustic system 800 may be an example of one implementation of acoustic system 200 in FIG. 2. In this illustrative example, acoustic system 800 is implemented in airport environment 802.

Microphone array 804 may be located near runway 806 in airport environment 802. Aircraft 808 may be located on a portion of runway 806. In this illustrative example, the engines of aircraft 808 are emitting acoustic emission 810.

Microphone array 804 detects the broadband spectrum of acoustic emission 810, which contains the entire range of frequencies contained in acoustic emission 810. On-site signal processor 812 receives the acoustic data from microphone array 804 including the broadband spectrum information for acoustic emission 810. On-site signal processor 812 may be an example of one implementation of site processing 502 in FIG. 5. In this illustrative example, signal processing is performed at microphone array 804 with the results being transmitted to a processing device, such as processing device 232 in FIG. 2, or central node processor 504 in FIG. 5, for example. In another advantageous embodiment, this signal processing may be performed at a central node, such as processing device 232 in FIG. 2, or central node processor 504 in FIG. 5, for example.

The acoustic data for acoustic emission 810 is received by on-site signal processor 812 and undergoes acoustic data conditioning 814. Acoustic data conditioning 814 is an example of one implementation of the processing that occurs by acoustic data conditioning 503 in FIG. 5. Spectral estimation 816 may process the narrowband portion and broadband spectrum of acoustic emission 810, and produce spectral estimation data 824. Bearing calculation 818 may process the narrowband portion and broadband spectrum of acoustic emission 810, and produce bearing estimation data 826. In this illustrative example, narrowband signature 819 is detected during processing of acoustic emission 810. As a result, spectral estimation 816 determines that the engines are being run up, or are increasing in revolutions per minute. Bearing calculation 818 determines that the bearing for aircraft 808 is constant. In other words, the aircraft is stationary and the engines are being run up.

This processing of acoustic data for acoustic emission 810 may be done during time segment 820. Segment 820 represents a segment of time between the forty second and forty-six second mark depicted in bearing versus time chart 822. This detection occurs while aircraft 808 is stationary, prior to any movement from aircraft 808. In other words, segment 820 represents the advance time in which an indication of movement by aircraft 808 may be generated and displayed to a user, such as an air traffic controller. In an advantageous embodiment, an air traffic controller may be given six extra seconds to respond to a potential movement by aircraft 808 before any actual movement occurs. As a result, response time is increased and potential conflicts may be more easily avoided.

The different components illustrated for acoustic system 800 are not meant to provide architectural limitations to the manner in which different embodiments may be implemented. The different advantageous embodiments may be implemented including components in addition to or in place of those illustrated for acoustic system 800. Other components shown in FIG. 8 can be varied from the illustrative examples shown.

Figure 9:
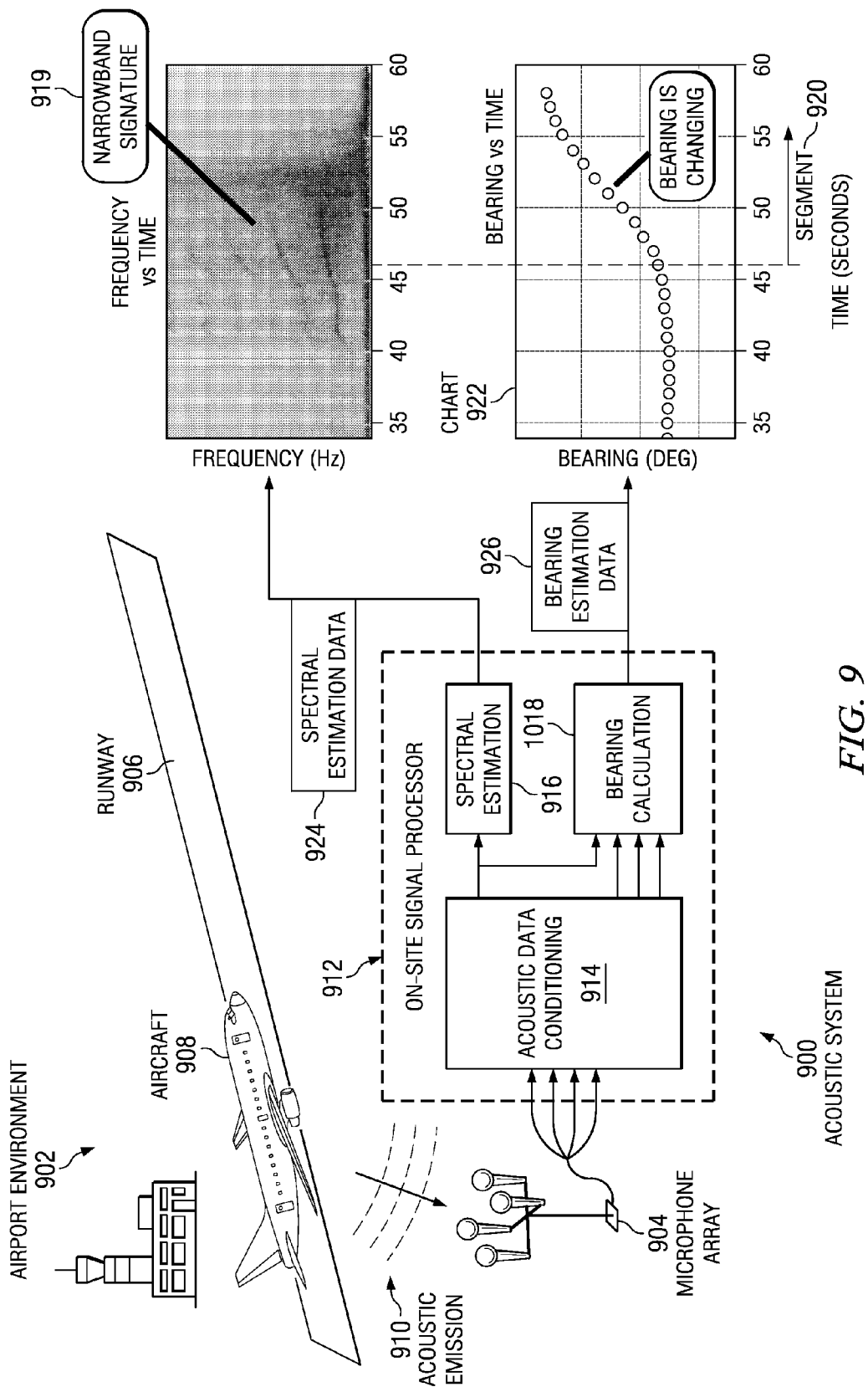

With reference now to FIG. 9, a diagram illustrating the detection of an aircraft with increasing engine revolutions per minute is depicted in accordance with an advantageous embodiment. Acoustic system 900 may be an example of one implementation of acoustic system 200 in FIG. 2. In this illustrative example, acoustic system 900 is implemented in airport environment 902.

Microphone array 904 may be located near runway 906 in airport environment 902. Aircraft 908 may be located on a portion of runway 906. In this illustrative example, the engines of aircraft 908 are emitting acoustic emission 910.

Microphone array 904 detects the broadband spectrum of acoustic emission 910, which contains the entire range of frequencies contained in acoustic emission 910. On-site signal processor 912 receives the acoustic data from microphone array 904 including the broadband spectrum information for acoustic emission 910. On-site signal processor 912 may be an example of one implementation of site processing 502 in FIG. 5. In this illustrative example, signal processing is performed at microphone array 904 with the results being transmitted to a processing device, such as processing device 232 in FIG. 2, or central node processor 504 in FIG. 5, for example. In another advantageous embodiment, this signal processing may be performed at a central node, such as processing device 232 in FIG. 2, or central node processor 504 in FIG. 5, for example.

The acoustic data for acoustic emission 910 is received by on-site signal processor 912 and undergoes acoustic data conditioning 914. Acoustic data conditioning 914 is an example of one implementation of the processing that occurs by acoustic data conditioning 503 in FIG. 5. Spectral estimation 916 may process the narrowband portion and broadband spectrum of acoustic emission 910, and produce spectral estimation data 924. Bearing calculation 918 may process the narrowband portion and broadband spectrum of acoustic emission and produce bearing estimation data 926. In this illustrative example, narrowband signature 919 is detected, and is determined to be shifted up in frequency, during processing of acoustic emission 910. As a result, spectral estimation 916 determines that the engines are increasing in revolutions per minute because the frequencies and power levels of the turbine lines are increasing. Bearing calculation 918 determines that the bearing for aircraft 908 with reference to microphone array 904 is changing. In other words, the aircraft is moving down runway 906, for example. Bearing calculation 918 may also determine the direction of bearing for aircraft 908 as one or more microphone arrays receive acoustic data for aircraft 908.

This processing of acoustic data for acoustic emission 910 may be done during time segment 920. Segment 920 represents a segment of time after the forty-six second mark depicted in bearing versus time chart 922. This detection occurs once aircraft 908 begins to move.

The different components illustrated for acoustic system 900 are not meant to provide architectural limitations to the manner in which different embodiments may be implemented. The different advantageous embodiments may be implemented including components in addition to or in place of those illustrated for acoustic system 900. Other components shown in FIG. 9 can be varied from the illustrative examples shown.

Figure 10:
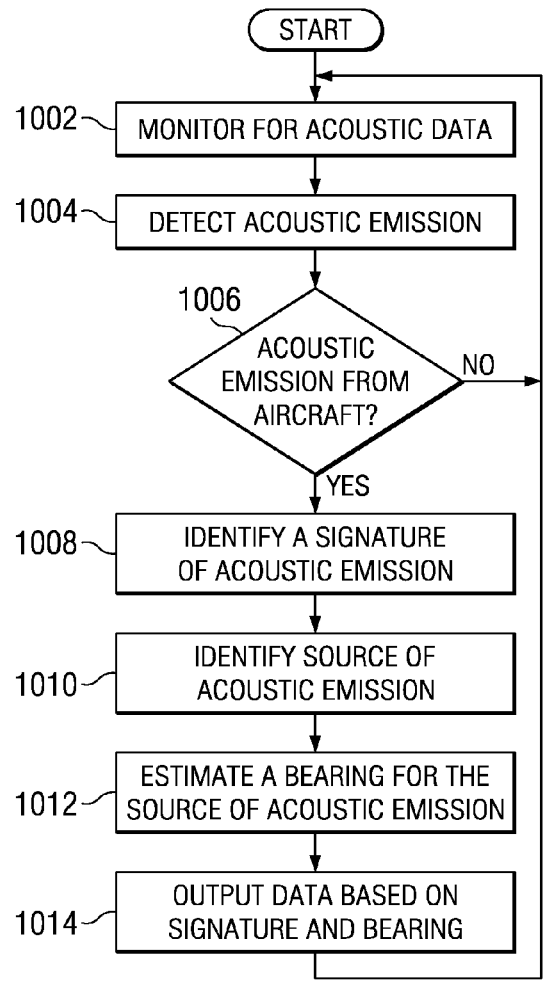
FIG. 10 is a flowchart illustrating a process for processing sound data in accordance with an advantageous embodiment.

With reference now to FIG. 10, a flowchart illustrating a process for processing sound data is depicted in accordance with an advantageous embodiment. The process in FIG. 10 may be implemented in a component such as processing device 232 in acoustic system 200, or site processing 502 in acoustic system 500, for example.

The process begins by monitoring for acoustic data (operation 1002). This acoustic data may be, for example, acoustic data 511 in FIG. 5. Monitoring is performed using a number of acoustic sensors, such as number of acoustic sensors 206 in FIG. 2, for example. The process detects an acoustic emission (operation 1004). The acoustic emission may be any type of sound detected by an acoustic sensor, including noise, for example.

Next the process determines whether the acoustic emission is from an aircraft (operation 1006). This determination may be made using stored signatures and frequencies in a database, such as classification database 236 in FIG. 2, for example. In an illustrative example, a detected acoustic emission may be compared against a number of known signatures and/or a number of turbine rotational frequencies in order to determine whether the acoustic emission is from an aircraft. If an acoustic emission is not from an aircraft, the process returns to operation 1002.

If the acoustic emission is from an aircraft, the process identifies a signature from the acoustic emission (operation 1008). In operation 1008, the signature may be a narrowband signature in these examples. This signature also may be shifted or un-shifted depending on the location of the aircraft relative to the acoustic sensor.

The process then identifies the source of the acoustic emission (operation 1010). The source may be identified by comparing the identified signature from the acoustic emission to a number of stored signatures in a classification database, such as classification database 236 in FIG. 2, for example.

Then the process estimates a bearing for the source of the acoustic emission (operation 1012). The bearing may be estimated based on shifted frequency for the signature identified in operation 1008. The process outputs data based on the identified signature and bearing estimation (operation 1014) and returns to operation 1002. The data outputted by process 1000 may be sent to a user interface, such as user interface 244 in FIG. 2, for example. In another illustrative example, the data may be stored in a storage device, such as data storage device 234 in FIG. 2, for example.

Figure 11:
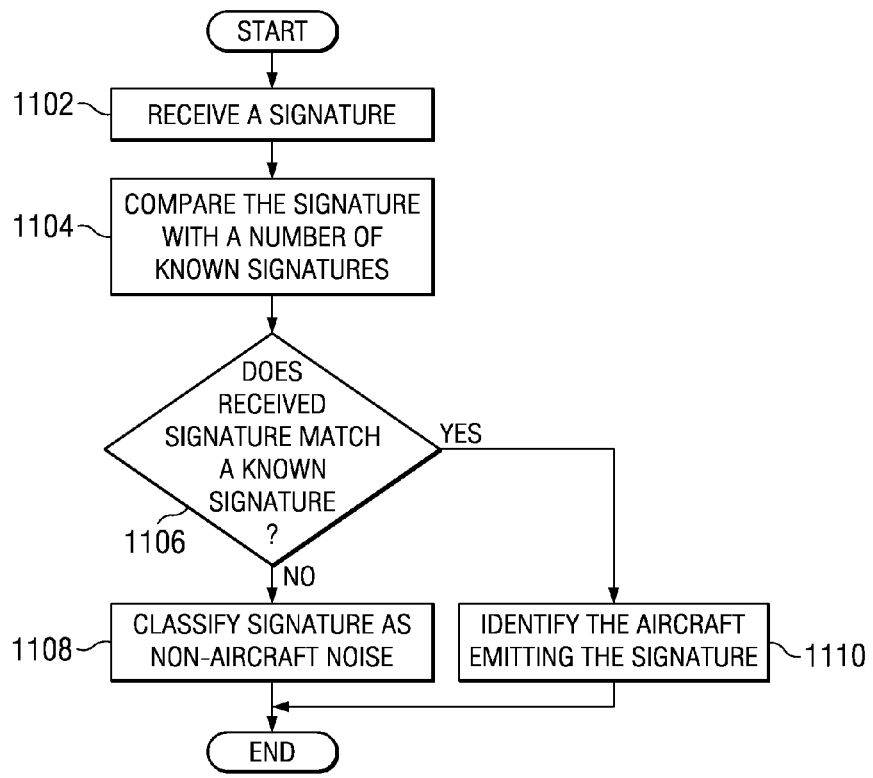
FIG. 11 is a flowchart illustrating a process for identifying a vehicle from sound data in accordance with an advantageous embodiment.

With reference now to FIG. 11, a flowchart illustrating a process for identifying a vehicle from sound data is depicted in accordance with an advantageous embodiment. The process illustrated in FIG. 11 may be implemented by a component such as classification 512 in FIG. 5, for example.

The process begins by receiving a signature (operation 1102). The signature may be a narrowband signature identified during processing of acoustic data, such as in site processing 502 in FIG. 5, for example. The process compares the signature with a number of known signatures (operation 1104). The number of known signatures may be stored in a database, for example, such as classification database 236 in FIG. 2 or database 516 in FIG. 5.

Next, the process determines whether the received signature matches a known signature (operation 1106). If the received signature does not match a known signature, the process classifies the received signature as non-aircraft noise (operation 1108), with the process terminating thereafter. If the received signature matches a known signature, the process identifies the aircraft emitting the signature (operation 1110), with the process terminating thereafter.

Figure 12:
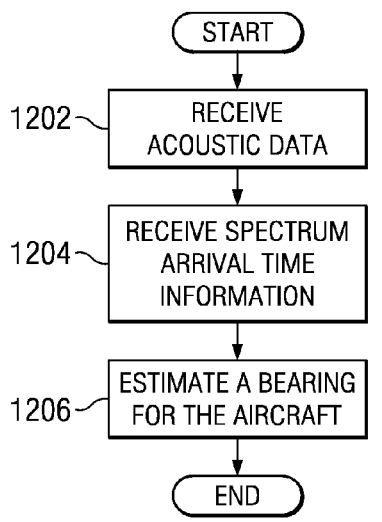
FIG. 12 is a flowchart illustrating a process for estimating a bearing of a vehicle in accordance with an advantageous embodiment.

With reference now to FIG. 12, a flowchart illustrating a process for estimating a bearing of a vehicle is depicted in accordance with an advantageous embodiment. The process in FIG. 12 may be implemented in a component such as position estimation 514 in FIG. 5, for example.

The process begins by receiving acoustic data (operation 1202). In these examples, the acoustic data includes frequency and amplitude of sound over time. This data also may include slant range and altitude at the closest point of approach. In an illustrative example, the data may provide slant range and altitude for an aircraft landing on or taking off a runway, for example.

The process receives spectrum arrival time information (operation 1204). In one illustrative example, spectrum arrival time information may include information about the particular acoustic sensors in a cluster array that detected the acoustic emission first, second, third, fourth, and so on. In another illustrative example, spectrum arrival time information may include information about the particular acoustic sensors in a cluster array that detected the highest spectrum level in the acoustic emission first, second, third, fourth, and so on.

The process then estimates a bearing for the aircraft (operation 1206), with the process terminating thereafter.

Figure 13:
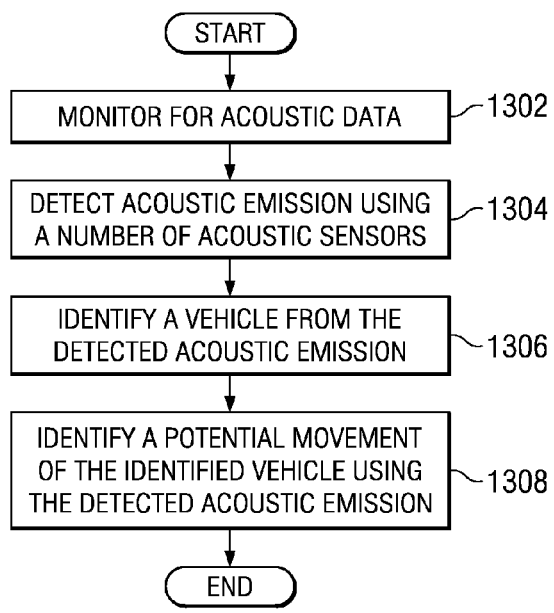
FIG. 13 is a flowchart illustrating a process for predicting movement of a vehicle in accordance with an advantageous embodiment.

With reference now to FIG. 13, a flowchart illustrating a process for predicting movement of a vehicle is depicted in accordance with an advantageous embodiment. The process in FIG. 13 may be implemented in a component such as processing device 232 in acoustic system 200, or site processing 502 in acoustic system 500, for example.

The process begins by monitoring for acoustic data (operation 1302). The process detects an acoustic emission using a number of acoustic sensors (operation 1304). The acoustic emission may be emitted by a vehicle, for example, such as aircraft 201 in FIG. 2 emitting acoustic emission 203.

Next, the process classifies a vehicle from the detected acoustic emission (operation 1306). The process may use a database of known acoustic signatures in order to classify the vehicle, such as classification database 236 in FIG. 2, for example. The vehicle may be classified by type of vehicle, such as an aircraft, and may further be classified by specific model of vehicle, such as a twin-engine jet aircraft or a Cessna 182, for example.

The process then predicts a potential movement of the classified vehicle using the detected acoustic emission (operation 1308), with the process terminating thereafter.

The potential movement may be predicted by a processing device, such as processing device 232 in FIG. 2 for example, examining the frequency spectrum of the acoustic emission. The frequency lines related to turbine rotational frequencies that appear at the onset of engine run-up are high frequency lines that can be distinguished from low frequency lines of an idling engine. The processing device may examine the frequency spectrum received from the acoustic data for an acoustic emission and predict a potential movement of the vehicle emitting the acoustic emission prior to any actual movement by the vehicle.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

The number of different advantageous embodiments provide a method, apparatus, and computer program product for detecting an aircraft. The different advantageous embodiments may provide a method for detecting an acoustic emission emitted by the aircraft using a number of acoustic sensors to form a detected acoustic emission. The aircraft may be identified from the detected acoustic emission to form an identified aircraft. A bearing may be estimated for the identified aircraft using the detected acoustic emission.

The number of different advantageous embodiments may further provide for a method and apparatus for detecting an aircraft. In one advantageous embodiment, a method is provided for detecting and tracking an aircraft. An acoustic emission is detected using a number of acoustic sensors. A signature from the acoustic emission is identified to form an identified signature. A source of the acoustic emission is identified using the identified signature to form an identified source. A bearing is estimated for the identified source of the acoustic emission to form an estimated bearing. A message is generated based on the identified signature and the estimated bearing for the source of the acoustic emission.

In another advantageous embodiment, an apparatus comprises a number of acoustic sensors and a data processing system. The number of acoustic sensors is capable of detecting an acoustic emission from an aircraft. The data processing system is in communication with the number of acoustic sensors and is capable of monitoring for the acoustic emission from the aircraft and estimating a bearing of the aircraft using acoustic data for the acoustic emission.

In this manner, the different advantageous embodiments are capable of providing a system for detecting and tracking aircraft for the purpose of runway safety and to support operation of small airports without air traffic control towers. This system may detect aircraft when other detection systems, such as radar systems, are unable to detect an aircraft. For example, an aircraft that is not moving or is stationary may not be detected by a conventional radar system in an airport environment.

Acoustic surveillance system 100 in FIG. 1 may complement other detection systems to provide identification of movement for aircraft. The Doppler tracking technique, in the advantageous embodiments, may be enhanced through more advanced processing to determine the time difference of arrival of the acoustic emission at the various sensors.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

Furthermore, the different embodiments can take the form of a computer program product accessible from a computer-usable or computer-readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer-usable or computer-readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments.

The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for detecting an aircraft, the method comprising:
    detecting, by one or more processors, an acoustic emission emitted by the aircraft using a number of acoustic sensors to form detected acoustic emission;
    identifying the aircraft from the detected acoustic emission to form an identified aircraft;
    estimating a bearing for the identified aircraft using the detected acoustic emission; and
    predicting, before a movement of the identified aircraft from a first position to a second position, a potential movement of the identified aircraft from the first position to the second position using the detected acoustic emission by identifying a change in the detected acoustic emission from a previous detected acoustic emission as a change from an idle state of the engine to a run up state of the engine.

2. A method for detecting an aircraft operating in an airport environment, the method comprising:
    detecting, by a processor, an acoustic emission using a number of acoustic sensors;
    identifying a signature from the acoustic emission to form an identified signature;
    identifying a source of the acoustic emission using the identified signature to form an identified source;
    estimating a change in bearing for the identified source of the acoustic emission to form an estimated bearing by identifying a change in the detected acoustic emission from a previous detected acoustic emission as a change from an idle state of the engine to a run up state of the engine; and
    generating a message based on the identified signature and the estimated bearing for the source of the acoustic emission;
    wherein the number of acoustic sensors include a number of global positioning system receivers capable of providing a timestamp for the acoustic emission detected by the number of acoustic sensors, and wherein each acoustic sensor in the number of acoustic sensors includes a global positioning system receiver of the number of global positioning system receivers;
    wherein the number of acoustic sensors provide acoustic data about the acoustic emission detected, and wherein the timestamp is included in the acoustic data for the acoustic emission.

3. The method of claim 2, further comprising:
    predicting, before a movement of the identified aircraft from a first position to a second position, a potential movement of the identified aircraft from the first position to the second position using the detected acoustic emission by identifying a change in the detected acoustic emission from a previous detected acoustic emission as a change from an idle state of the engine to a run up state of the engine;
    wherein the number of acoustic sensors further comprise at least one microphone array cluster.

4. The method of claim 3, wherein the at least one microphone array cluster includes at least four acoustic sensors.

5. The method of claim 2, wherein identifying the signature from the acoustic emission further comprises:
   detecting a narrowband frequency within a broadband spectrum for the acoustic emission, wherein the narrowband frequency forms the identified signature.

6. The method of claim 2, wherein identifying the source of the acoustic emission further comprises:
   comparing the identified signature with a number of known signatures; and
   determining whether the identified signature is a match with at least one signature in the number of known signatures.

7. The method of claim 6, further comprising:
   responsive to a determination that the identified signature is a match with the at least one signature in the number of known signature, identifying the source of the identified signature to form an identified source.

8. The method of claim 6, further comprising:
   responsive to a determination that the identified signature is not a match with any signature in the number of known signature, classifying the identified signature as non-aircraft noise.

9. The method of claim 2, wherein estimating the bearing for the identified source of the acoustic emission further comprises:
   receiving acoustic data for the acoustic emission;
   receiving spectrum arrival time information, wherein the spectrum arrival time information includes information about the specific time an individual acoustic sensor in the number of acoustic sensors detected the acoustic emission; and
   estimating the bearing for the identified source based on the spectrum arrival time information.

10. The method of claim 2, wherein generating the message based on the identified signature and the estimated bearing further comprises:
    sending the message to a user interface, wherein the message is displayed as an alert in the user interface.

11. An apparatus comprising:
    a number of acoustic sensors capable of detecting a number of acoustic emissions from an aircraft;
    a data processing system in communication with the number of acoustic sensors, wherein the data processing system is capable of monitoring the number of acoustic sensors for the number of acoustic emissions from the aircraft and estimating a number of bearings of the aircraft using acoustic data for the number of acoustic emissions as the aircraft physically moves over a period time, and wherein the data processing system is capable of predicting, before a movement of the identified aircraft from a first position to a second position, a potential movement of the identified aircraft from the first position to the second position using the detected acoustic emission by identifying a change in the detected acoustic emission from a previous detected acoustic emission as a change from an idle state of the engine to a run up state of the engine;
    a number of global positioning system receivers capable of providing a number of timestamps for the number of acoustic emissions detected by the number of acoustic sensors, wherein each acoustic sensor in the number of acoustic sensors includes a global positioning system receiver of the number of global positioning system receivers; and
    wherein the number of acoustic sensors provide the number of acoustic data for the number of acoustic emissions to the data processing system, and wherein the number of timestamps are included in the acoustic data for the number of acoustic emissions by the number of global positioning system receivers.

12. The apparatus of claim 11, wherein the data processing system is capable of identifying a signature for the aircraft in a range of frequencies for the acoustic emission in response to detecting the acoustic emission by the number of acoustic sensors and is capable of identifying the aircraft from the signature.

13. The apparatus of claim 11, wherein the data processing system is capable of identifying a bearing of the aircraft from the acoustic emission.

14. The apparatus of claim 11, wherein the number of acoustic sensors are a number of omni-directional microphone array clusters.

15. The apparatus of claim 14, wherein an omni-directional microphone array cluster includes at least four individual acoustic sensors.

* * * * *